US006500452B2

(12) United States Patent
Smith, Jr. et al.

(10) Patent No.: US 6,500,452 B2
(45) Date of Patent: Dec. 31, 2002

(54) ENERGY-ENHANCING SUPPLEMENT

(75) Inventors: Edwin B. Smith, Jr., Pearland, TX (US); Lance Griffin, San Diego, CA (US)

(73) Assignee: E³ Limited, LLC., Carlsbad, CA (US)

( * ) Notice: Subject to any disclaimer, the term of this patent is extended or adjusted under 35 U.S.C. 154(b) by 99 days.

(21) Appl. No.: 09/812,776

(22) Filed: Mar. 15, 2001

(65) Prior Publication Data

US 2002/0168421 A1 Nov. 14, 2002

(51) Int. Cl.⁷ ............................................. A61K 47/00
(52) U.S. Cl. .................. 424/439; 424/400; 424/464; 424/484; 424/489; 424/195.15; 424/725; 424/755

(58) Field of Search .................. 424/400, 439, 424/464, 484, 489, 195.15, 725, 755

*Primary Examiner*—Thurman K. Page
*Assistant Examiner*—Charesse Evans
(74) *Attorney, Agent, or Firm*—Frank G. Morkunas

(57) ABSTRACT

A composition for a dietary supplement supplies components to increase the cellular formation of ATP, and thus provide energy for cellular activity. Active ingredients include 4-aminobenzoic acid, 4-hydroxybenzoic acid, L-cysteine, L-methionine, sodium molybdate, selenium, lithium bromide, horseradish powder, and shiitake mushroom powder. The composition of the present invention is administered in an oral dosage form to increase energy in humans.

20 Claims, No Drawings

ENERGY-ENHANCING SUPPLEMENT

FIELD OF THE INVENTION

The present invention relates to dietary supplements. More particularly, it relates to dietary supplements formulated to increase energy available in cells of humans. The present invention relates to a combination of enzymatic and metallo-enzymatic cofactors and nutritional additives to increase the synthesis of adenosine triphosphate (ATP) in human cells. This increase in cellular ATP produces greater energy levels in humans.

BACKGROUND OF THE INVENTION

A major source of energy for the human body is derived from foods being broken down and utilized through metabolic pathways. In one such pathway, energy is stored in storage molecules as fats and carbohydrates. In another pathway, the products resulting from the break down of foods can be metabolically and enzymatically processed. It happens that these processes take place in the mitochondria of cells during cellular respiration. The chemical energy released during this respiration is captured in the form of adenosine triphosphate (ATP). The ATP then delivers the energy to the location within a cell where energy-consuming activities are taking place. Since ATP does not store energy, when energy is needed by the cell, storage molecules, such as glycogen, are converted to ATP.

ATP is a nucleotide that consists of three parts: a nitrogenous base, adenine; a sugar, ribose; and a chain of three phosphate groups bound to the ribose. Available energy is contained in the bonds between these phosphates, and is released when the bonds are broken. The bonds are broken in the presence of a molecule of water in a process called hydrolysis. Usually, when hydrolysis occurs, one phosphate is removed from ATP to yield energy. ATP is thus converted to adenosine diphosphate (ADP). While cells continuously break down ATP to obtain energy, ATP is also being synthesized from ADP and phosphate. It can be appreciated that the complex pathways by which energy is made available in the form of ATP are mediated by enzymes.

Coupled with ATP synthesis is the oxidation of carbohydrates and lipids via the mitochondrial electron transport chain (ETC). The ETC, or respiratory chain, is the system by which electrons, from the reduced electron carriers of intermediary metabolism, are channeled to oxygen and protons to yield water ($H_2O$). The main components of the ETC are cofactors nicotinamide adenine dinucleotide (NAD) and its reduced form, NADH. The cofactors that participate in this process are flavin mononucleotide (FMN), flavin adenine dinucleotide (FAD), and nicotinamide adenine dinucleotide phosphate ($NADP^+$). Enzymes catalyze the oxidation and reduction of these cofactors. These enzymes are usually very selective toward a particular cofactor in a particular oxidative state. Electrons are effectively transported as hydride ions ($H^-$), which are formally equivalent to ($H^+ + 2e^-$).

The electron transport reactions for the respective cofactors can be expressed as follows:

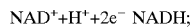

$NAD^+ + H^+ + 2e^-$ NADH;

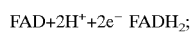

$FAD + 2H^+ + 2e^-$ $FADH_2$;

and

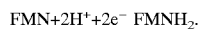

$FMN + 2H^+ + 2e^-$ $FMNH_2$.

In order for electron transport to take place, the cofactors interact with a series of complexes which enzymatically catalyze the reduction reactions. These complexes, designated complex I, II, III, and IV represent the stages of enzymatic reduction which transports electrons. The final stage of electron transport may be referred to as complex V. It is now generally accepted that the coupling of electron transport and ATP synthesis is brought about by the action of a proton electrochemical-potential gradient. This gradient arises as a consequence of the electron transport and is dissipated by ATP synthase to generate ATP by combining ADP and inorganic Phosphate ($P_i$). The organization of the electron transport chain in the mitochondria can be schematically represented as follows:

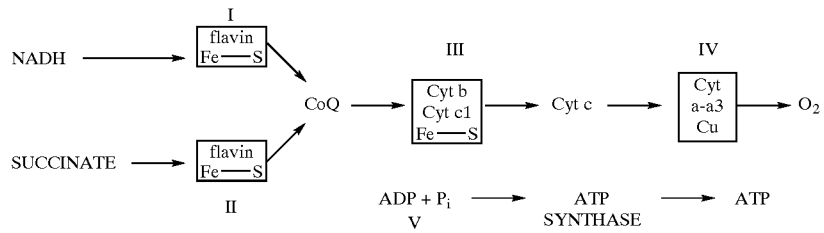

Basically, and without the introduction of the present invention, what occurs in complex I is that the molecule Coenzyme Q (CoQ or ubiquinone) undergoes reduction in its reaction with NADH to form reduced CoQ ($CoQH_2$). In a separate reaction, complex II mediates electron transfer from succinate to CoQ, forming FAD from $FADH_2$. As a result of these reactions, energy is transported to complex III. Complex III catalyzes electron transfer from reduced CoQ to a series of cytochromes. Cytochrome activity is in turn determined by the side chains on a porphyrin moiety which is the basis of the cytochrome molecule. Cytochrome c, for instance, requires a cysteine side chain on the porphyrin moiety for optimal function. It is known, however, that leucine and isoleucine can substitute for cysteine on this side chain. Electrons are channeled through complex IIII to CoQ by an iron-sulfur protein. In this iron sulfur protein, the iron atoms are bound to the porphyrin by a cysteine group and sulfide ions. At complex IV cytochrome activity produces oxygen ($O_2$) and creates a proton electrochemical-potential gradient. As mentioned above, this gradient is dissipated by ATP synthase in the formation of ATP from ADP and $P_i$.

Because ATP does not store energy, it would be desirable to provide a source of energy that is readily available for the production of ATP in a human subject. It would further be desirable to enhance the formation of ATP by providing a formulation that would act to accelerate the enzymatic reactions of the electron transport chain. Such a formulation would increase the energy level in a human subject and provide a feeling of well being.

In light of the above, it is an object of the present invention to provide a source of energy that is readily available for the formation of ATP in human cells. Another object of the present invention is to provide a formula for a dietary supplement that will enhance the action of the electron transport chain to carry electrons more readily for the formation of the ATP. Yet another object of the present invention is to provide a dietary supplement to increase energy levels in humans that is easily ingested, is safe, and is comparatively cost effective.

SUMMARY OF THE PREFERRED EMBODIMENTS

The present invention is directed to a composition for a dietary supplement designed to provide a source of energy that is readily available for the production of ATP in human cells. To that end, the composition of the present invention is formulated to supply components which will enhance the enzymatic activity of the ETC and thus allow for increased formation of ATP, which in turn will provide energy for cellular activity.

Metabolic activity resulting in increased energy results from the formulation of active ingredients in the present invention. These ingredients are: 4-aminobenzoic acid, 4-hydroxybenzoic acid, L-cysteine, L-methionine, sodium molybdate, selenium, lithium bromide, horseradish powder, and shiitake mushroom powder. The active ingredients are combined with an inactive carrier, such as magnesium silicate powder (talc) to form a product for oral administration.

The composition of the present invention works during mitochondrial respiration to enhance the activity of the respective complexes in the transport of electrons for the formation of ATP. For example, complex I, the NADH/ubiquinone complex, requires metal cofactors for enzymatic or metabolic activity. These metal cofactors may include lithium, molybdate, selenium, copper, iron, magnesium, and zinc in specialized tissues. The composition of the present invention contains selenium, sodium molybdate, and lithium bromide to accelerate this step. It is noted that substitution by other bivalent metallic ions, including Zn, Mn, Se, Cr, Te, Co, Ni, Mg, Ba, and Sr in the enzymatic pathways may occur with changed efficiency.

At the complex III phase, 4-hydroxybenzoic acid (POBA) and 4-aminobenzoic acid (PABA) enter the ETC by linkage to the cysteine side chain in the iron sulfur protein. This cysteine side chain can also be substituted by methionine. It is further known that side chain substitution occurs with the cytochromes. This substitution takes place on the porphyrin moiety, and is dependent on the type of cytochrome represented. Cytochrome c, for example, requires a cysteine side chain for optimal performance. Specifically, POBA acts at complex III to inhibit the production of protons. Inhibition of protons causes greater production of electrons for use in the conversion of complexes III and IV, resulting in the increased production of ATP. The end result is a greater source of energy for the user.

In the preferred embodiment, the composition of the present invention is administered in capsule form, preferably in the amount of from 500 to 1000 mg daily. At this dose, the composition supplies concentrations of ingredients that can increase energy in human subjects. It is envisioned that other dosage forms can be used. For example, chewable tablets, liquid, and powder formulations can be made to allow for faster absorption of the active ingredients.

DESCRIPTION OF THE PREFERRED EMBODIMENT

The composition of the present invention contains, as active ingredients: 4-aminobenzoic acid (approximately 20–80%), 4-hydroxybenzoic acid (approximately 10–50%), L-cysteine (approximately 0.1–10%), L-methionine (approximately 0.1–10%), sodium molybdate (approximately 0.1–5%), selenium (approximately 0.1–2%), lithium bromide (approximately 0.05–4%), horseradish powder (approximately 0.05–10%), and shiitake mushroom powder (approximately 0–10%). A nutritionally acceptable carrier can be used as an inactive ingredient to form an oral dosage form.

Use of the composition as formulated above has proven to increase the energy level of persons ingesting the composition. Best results, however, have occurred with formulations containing approximately 40% by weight 4-aminobenzoic acid, approximately 20% by weight 4-hydrooxybenzoic acid, approximately 4% by weight L-cysteine, approximately 2.7% by weight L-methionine, approximately 2% by weight sodium molybdate, approximately 0.002% by weight selenium, approximately 0.4% by weight lithium bromide, approximately 0.4% by weight freeze dried horseradish powder, approximately 0.4% by weight freeze dried shiitake mushroom powder, and approximately 30.098% by weight talc or other suitable carrier.

Specifically, the selenium is in the form of selenium oxide ($SeO_2$), and can be supplied from readily available selenium-containing amino acids. Examples of these amino acids are selenomethionine, selenocysteine, and selenohistidine. Further, the sodium molybdate of the composition can be substituted by any nutritionally acceptable salt of molybdic acid. In the preferred embodiment, the horseradish powder is the freeze-dried powder from the root of the horseradish. The shiitake mushroom is also in the form of a freeze-dried powder. The usual dosage form is a capsule with a total weight of approximately 500 mg. When a carrier is necessary to form capsules with this total weight, aluminum magnesium silicate (talc) is used. It is further preferred that the talc be in particles measuring from 5 to 8 microns in diameter.

The metabolic activity of the ingredients contained in the composition of the present invention is discussed above. It is known, for example, that metal cofactors are required at complex I of the electron transport chain (ETC). These cofactors are required for enzymatic activity and may include lithium, molybdate, selenium, copper, iron, magnesium, and zinc. The composition of the present invention contains selenium, sodium molybdate, and lithium bromide to accelerate this step. At the complex III phase, 4-hydroxybenzoic acid (POBA) and 4-aminobenzoic acid (PABA) enter the ETC by linkage to the cysteine side chain in the iron sulfur protein. This cysteine side chain can also be substituted by methionine. Cysteine and methionine are supplied by the composition of the present invention to aid the formation of these side chains. Side chain substitution also occurs at the cytochromes. This substitution takes place on the porphyrin moiety, and is dependent on the type of cytochrome represented. Cytochrome c, for example requires a cysteine side chain for optimal performance. It can be appreciated that the cysteine provided by the present invention accelerates ATP formation at cytochrome c level as well as at the iron sulfur protein. The inhibition of protons by POBA causes greater production of electrons for use in the conversion of complexes III and IV, resulting in the increased production of ATP. It can be appreciated that the end result of the activity of the ingredients of the present invention is a greater source of energy for the user.

To form the composition of the present invention, the ingredients are mixed preferably in a Hobart paddle mixer of sufficient size to hold a batch. These ingredients are added in the following order: 4-aminobenzoic acid, 4-hydroxybenzoic acid, L-cysteine, L-methionine, sodium molybdate, selenium-containing amino acid, lithium bromide, freeze dried horseradish powder from the root, freeze-dried shiitake mushroom powder, and sufficient talc to give 500 mg composition per capsule. The resulting powder mixture is mixed at low speed, avoiding dusting, for a minimum of five minutes to a maximum of ten minutes. It is crucial that the mixing be complete and without stratification.

Although the size of the batch is not important, the ratio of ingredients to each other and complete mixing without stratification is critical to the formation of the composition.

The approximate ratios of active ingredients are as follows: 2 parts 4-aminobenzoic acid to 1 part 4-hydroxybenzoic acid; 4 parts L-cysteine to 2.7 parts L-methionine; 10 parts 4-aminobenzoic acid to 1 part L-cysteine; 2 parts L-cysteine to 1 part sodium molybdate; 5 parts sodium molybdate to 1 part lithium bromide; 5 parts sodium molybdate to 1 part horseradish powder; and 5 parts sodium molybdate to 1 part shiitake mushroom powder.

While the preferred embodiment of the present invention is in a capsule form, it is envisioned that other dosage forms can be made. These dosage forms may include chewable tablets and liquids, which may give faster absorption than the capsule form.

TABLE 1

TEST RESULTS
% of Disability

| Conditions | Before Using $E^3$ % | After Taking $E^3$ For: | | | Discontinued $E^3$ For: | | |
|---|---|---|---|---|---|---|---|
| | | 1 week | 2 week | 1 month | 1 week | 2 week | 1 month |
| Subject 1: Age 53 Sex F | | | | | | | |
| Chronic Fatigue Syndrome | 85 | 80 | 80 | 75 | | | |
| Brain Fog | 80 | 70 | 65 | 50 | | | |
| Decreased Physical Energy | 75 | 70 | 65 | 55 | | | |
| Decreased Mental Energy | 90 | 80 | 75 | 60 | | | |
| Impaired Mental Acuity | 90 | 80 | 75 | 60 | | | |
| Impaired Clarity of Thought | 80 | 70 | 65 | 60 | | | |
| Impaired Memory Recall | 75 | 65 | 60 | 55 | | | |
| Decreased Muscle Tone | 40 | 40 | 35 | 30 | | | |
| Impaired Sense of Wellbeing and Calm | 60 | 55 | 55 | 45 | | | |
| Decreased Food Utilization and Elimination | 75 | 75 | 70 | 60 | | | |
| Decreased Appetite | 60 | 60 | 55 | 50 | | | |
| Subject 2: Age 70 Sex M | | | | | | | |
| Brain Fog | 0 | 0 | 0 | | | | |
| Mental Exhaustion | 20 | 15 | 10 | | | | |
| Decreased Physical Energy | 50 | 40 | 10 | | | | |
| Decreased Mental Energy | 10 | 5 | 5 | | | | |
| Impaired Mental Acuity | 10 | 5 | 5 | | | | |
| Impaired Clarity of Thought | 10 | 5 | 5 | | | | |
| Impaired Memory Recall | 30 | 25 | 20 | | | | |
| Decreased Muscle Tone | 50 | 50 | 50 | | | | |
| Impaired Sense of Wellbeing and Calm | 5 | 5 | 5 | | | | |
| Decreased Food Utilization and Elimination | 0 | 0 | 0 | | | | |
| Decreased Appetite | 0 | 0 | 0 | | | | |
| Subject 3: Age 27 Sex M | | | | | | | |
| Brain Fog | 40 | 38 | 30 | 15 | 30 | | |
| Mental Exhaustion | 60 | 52 | 44 | 26 | 44 | | |
| Decreased Physical Energy | 70 | 60 | 50 | 25 | 50 | | |
| Decreased Mental Energy | 60 | 52 | 44 | 26 | 44 | | |
| Impaired Mental Acuity | 60 | 52 | 44 | 26 | 44 | | |
| Impaired Clarity of Thought | 70 | 60 | 50 | 25 | 50 | | |
| Impaired Memory Recall | 70 | 60 | 50 | 25 | 50 | | |
| Decreased Muscle Tone | 40 | 38 | 30 | 15 | 30 | | |
| Impaired Sense of Wellbeing and Calm | 80 | 70 | 60 | 25 | 60 | | |
| Decreased Food Utilization and Elimination | 80 | 70 | 60 | 25 | 60 | | |
| Decreased Appetite | 80 | 70 | 60 | 25 | 60 | | |
| Subject 4: Age 31 Sex F | | | | | | | |
| Depression | 70 | 60 | 50 | 5 | 70 | | |
| Brain Fog | 90 | 90 | 80 | 30 | 50 | | |
| Mental Exhaustion | 90 | 80 | 60 | 10 | 60 | | |
| Decreased Physical Energy | 70 | 80 | 60 | 10 | 70 | | |
| Decreased mental Energy | 90 | 80 | 50 | 10 | 90 | | |
| Impaired Mental Acuity | 60 | 50 | 50 | 15 | 60 | | |

TABLE 1-continued

TEST RESULTS
% of Disability

| Conditions | Before Using $E^3$ % | After Taking $E^3$ For: | | | Discontinued $E^3$ For: | | |
|---|---|---|---|---|---|---|---|
| | | 1 week | 2 week | 1 month | 1 week | 2 week | 1 month |
| Impaired Clarity of Thought | 80 | 50 | 40 | 5 | 80 | | |
| Impaired Memory Recall | 60 | 50 | 40 | 5 | 60 | | |
| Decreased Muscle Tone | 60 | 30 | 20 | 5 | 60 | | |
| Impaired Sense of Wellbeing and Calm | 60 | 50 | 20 | 20 | 60 | | |
| Decreased Food Utilization and Elimination | 80 | 70 | 60 | 30 | 80 | | |
| Decreased Appetite | 80 | 70 | 60 | 20 | 80 | | |
| Subject 5: Age 43 Sex F | | | | | | | |
| Chronic Fatigue Syndrome | 80 | 80 | 75 | 60 | 75 | 80 | |
| Brain Fog | 80 | 75 | 65 | 45 | 60 | 75 | |
| Decreased Physical Energy | 75 | 65 | 60 | 50 | 65 | 75 | |
| Decreased Mental Energy | 65 | 60 | 55 | 45 | 55 | 65 | |
| Impaired Mental Acuity | 50 | 45 | 40 | 30 | 45 | 50 | |
| Impaired Clarity of Thought | 75 | 65 | 60 | 40 | 55 | 65 | |
| Impaired Memory Recall | 75 | 70 | 65 | 50 | 65 | 75 | |
| Decreased Muscle Tone | 65 | 65 | 55 | 45 | 60 | 65 | |
| Impaired Sense of Wellbeing and Calm | 60 | 55 | 50 | 40 | 55 | 60 | |
| Decreased Food Utilization and Elimination | 65 | 65 | 55 | 45 | 60 | 65 | |
| Decreased Appetite | 70 | 70 | 60 | 50 | 65 | 70 | |
| Subject 6: Age 62 Sex M | | | | | | | |
| Impaired Mental Acuity | 95 | | 90 | 1 | | | |
| Impaired Memory Recall | 90 | | 1 | 1 | | | |
| Decreased Muscle Tone | 90 | | 2 | 1 | | | |
| Subject 7: Age 36 Sex F | | | | | | | |
| Mental Exhaustion | 25 | 22 | 16 | 7 | | | |
| Impaired Mental Acuity | 10 | 8 | 3 | 1 | | | |
| Decreased Muscle Tone | 20 | 15 | 9 | 4 | | | |
| Decreased Appetite | 15 | 12 | 7 | 3 | | | |
| Subject 8: Age 37 Sex F | | | | | | | |
| Mental Exhaustion | 30 | 20 | 15 | 10 | | | |
| Decreased Physical Energy | 60 | 40 | 30 | 10 | | | |
| Decreased Mental Energy | 40 | 20 | 0 | 0 | | | |
| Impaired Sense of Wellbeing and Calm | 50 | | | 100 | | | |
| Decreased Appetite | | | | | | | |
| Subject 9: Age 30 Sex F | | | | | | | |
| Mental Exhaustion | 30 | 25 | 15 | 7 | | | |
| Decreased Physical Energy | 15 | 10 | 7 | 3 | | | |
| Decreased Mental Energy | 20 | 15 | 9 | 3 | | | |
| Impaired Mental Acuity | 10 | 7 | 4 | 1 | | | |
| Decreased Muscle Tone | 20 | 18 | 12 | 6 | | | |
| Decreased Appetite | 15 | 12 | 8 | 3 | | | |
| Subject 10: Age 22 Sex F | | | | | | | |
| Decreased Physical Energy | 10 | 5 | 3 | 0 | | | |
| Impaired Memory Recall | 10 | 5 | 3 | 0 | | | |
| Decreased Appetite | 10 | 5 | 3 | 1 | | | |

Table I records test results logged by ten subjects who ingested the energy-enhancing supplement of the present invention ($E^3$). Specifically, the subjects included both males and females, ranging from 22 to 70 years of age. All of the subjects ingested 500 mg of the supplement twice daily.

At the beginning of the test period, the subjects rated their disability based on the conditions listed in the first column of Table I. The percentages recorded in the second column of Table I, "Before Using $E^3$", indicate the extent of disability for each condition listed. The percentages recorded in the second column were recorded before the subjects began taking the supplement, and thus represent baseline figures for the respective conditions.

Subjects continued ingesting the supplement, and their condition was monitored and recorded on a weekly basis. The third and fourth columns indicate reported percentages of disability for each subject at one week and at two weeks. The fifth column shows reported disability for each subject after each subject has ingested the supplement for one month.

The subjects discontinued taking the supplement after one month. The subjects continued to report their percentage of disability for the listed conditions intervals of one week. For those subjects who have reported results, the percentage of disability for the listed conditions has increased when the supplement has been discontinued.

While the particular composition as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A composition for supplying energy for ATP synthesis in humans comprising as active ingredients, 4-aminobenzoic acid, 4-hydroxybenzoic acid, L-cysteine, L-methionine, sodium molybdate, selenium, lithium bromide, horseradish powder, shiitake mushroom powder, said active ingredients being combined with a nutritionally acceptable carrier as an inactive ingredient for oral administration.

2. The composition of claim 1 wherein said selenium is $SeO_2$.

3. The composition of claim 1 wherein said selenium is selected from a group of selenium-containing amino acids consisting of: selenomethionine, selenohistidine and selenocysteine.

4. The composition of claim 1 wherein said carrier is aluminum magnesium silicate powder, said powder having particles, each of said particles having a diameter measuring approximately 5 to 8 microns.

5. The composition of claim 1 wherein said horseradish powder is a freeze-dried horseradish powder.

6. The composition of claim 1 wherein said shiitake mushroom powder is a freeze dried shiitake mushroom powder.

7. The composition of claim 1 wherein said sodium molybdate may be substituted by a molybdate salt selected from a group consisting of the salts of molybdic acid.

8. The composition of claim 1, comprising:
   4-aminobenzoic acid, between approximately 20 and approximately 80 percent by weight;
   4-hydroxybenzoic acid, between approximately 10 and approximately 50 percent by weight;
   L-cysteine, between approximately 0.1 and approximately 10 percent by weight;
   L-methionine, between approximately 0.1 and approximately 10 percent by weight;
   sodium molybdate, between approximately 0.1 and approximately 5 percent by weight;
   selenium, between approximately 0.1 and approximately 2.0 percent by weight
   lithium bromide, between approximately 0.05 and approximately 4 percent by weight;
   horseradish powder, between approximately 0.05 and approximately 10 percent by weight;
   shiitake mushroom powder, between approximately 0 and approximately 10 percent by weight; and
   said carrier, between approximately 0 and approximately 31 percent by weight.

9. The composition of claim 1 wherein the active and inactive ingredients are combined in percentages of the total weight of the composition, said composition comprising:
   4-aminobenzoic acid, approximately 40 percent;
   hydroxybenzoic acid, approximately 20 percent;
   L-cysteine, approximately 4 percent;
   methionine, approximately 2.7 percent;
   sodium molybdate, approximately 2 percent;
   selenium, approximately 0.002 percent;
   lithium bromide, approximately 0.4 percent;
   horseradish powder, approximately 0.4 percent;
   shiitake mushroom powder, approximately 0.4 percent; and
   said carrier, approximately 30.098 percent.

10. The composition of claim 1, comprising:
    approximately 2 parts 4-aminobenzoic acid to approximately 1 part 4-hydroxybenzoic acid;
    approximately 4 parts L-cysteine to approximately 2.7 parts L-methionine;
    approximately 10 parts 4-aminobenzoic acid to approximately 1 part L-cysteine;
    approximately 2 parts L-cysteine to approximately 1 part sodium molybdate;
    approximately 5 parts sodium molybdate to approximately 1 part lithium bromide;
    approximately 5 parts sodium molybdate to approximately 1 part horseradish powder; and
    approximately 5 parts sodium molybdate to approximately 1 part shiitake mushroom powder.

11. A composition for a nutritional supplement useful for increasing energy in humans, said composition comprising active ingredients 4-aminobenzoic acid, 4-hydroxybenzoic acid, L-cysteine, L-methionine, sodium molybdate, selenium, lithium bromide, horseradish powder, shiitake mushroom powder, said active ingredients being combined with a nutritionally acceptable carrier as an inactive ingredient for oral administration.

12. The composition of claim 11 wherein said selenium is $SeO_2$.

13. The composition of claim 11 wherein said selenium is selected from a group of selenium-containing amino acids consisting of:
    selenomethionine, selenocysteine, and selenohistidine.

14. The composition of claim 11 wherein said carrier is aluminum magnesium silicate powder, said powder having particles, each of said particles having a diameter measuring approximately 5 to 8 microns.

15. The composition of claim 11 wherein said horseradish powder is a freeze-dried horseradish powder.

16. The composition of claim 11 wherein said shiitake mushroom powder is a freeze dried shiitake mushroom powder.

17. The composition of claim 11 wherein said sodium molybdate may be substituted by a molybdate salt selected from a group consisting of the salts of molybdic acid.

18. The composition of claim 11, comprising:
    4-aminobenzoic acid, between approximately 20 and approximately 80 percent by weight;
    4-hydroxybenzoic acid, between approximately 10 and approximately 50 percent by weight;
    L-cysteine, between approximately 0.1 and approximately 10 percent by weight;
    L-methionine, between approximately 0.1 and approximately 10 percent by weight;
    sodium molybdate, between approximately 0.1 and approximately 5 percent by weight;
    selenium, between approximately 0.1 and approximately 2.0 percent by weight;
    lithium bromide, between approximately 0.05 and approximately 4 percent by weight;
    horseradish powder, between approximately 0.05 and approximately 10 percent by weight;

shiitake mushroom powder, between approximately 0 and approximately 10 percent by weight; and said carrier, between approximately 0 and approximately 31 percent by weight.

19. The composition of claim 11, wherein the active and inactive ingredients are combined in percentages of the total weight of the composition, said composition comprising:

4-aminobenzoic acid, approximately 40 percent;
hydroxybenzoic acid, approximately 20 percent;
L-cysteine, approximately 4 percent;
methionine, approximately 2.7 percent;
sodium molybdate, approximately 2 percent;
selenium, approximately 0.002 percent;
lithium bromide, approximately 0.4 percent;
horseradish powder, approximately 0.4 percent;
shiitake mushroom powder, approximately 0.4 percent; and
said carrier, approximately 30.098 percent.

20. The composition of claim 11, comprising:

approximately 2 parts 4-aminobenzoic acid to approximately 1 part 4-hydroxybenzoic acid;

approximately 4 parts L-cysteine to approximately 2.7 parts L-methionine;

approximately 10 parts 4-aminobenzoic acid to approximately 1 part L-cysteine;

approximately 2 parts L-cysteine to approximately 1 part sodium molybdate;

approximately 5 parts sodium molybdate to approximately 1 part lithium bromide;

approximately 5 parts sodium molybdate to approximately 1 part horseradish powder; and approximately 5 parts sodium molybdate to approximately 1 part shiitake mushroom powder.

* * * * *